US012721652B1

(12) United States Patent
Attum

(10) Patent No.: US 12,721,652 B1
(45) Date of Patent: Sep. 1, 2026

(54) SINGLE-PENETRATION SHEATH FOR MINIMALLY INVASIVE MEDICAL PROCEDURES

(71) Applicant: Basem Abdulia Attum, Los Osos, CA (US)

(72) Inventor: Basem Abdulia Attum, Los Osos, CA (US)

(*) Notice: Subject to any disclaimer, the term of this patent is extended or adjusted under 35 U.S.C. 154(b) by 248 days.

(21) Appl. No.: 18/372,292

(22) Filed: Sep. 25, 2023

Related U.S. Application Data

(60) Provisional application No. 63/419,043, filed on Oct. 25, 2022.

(51) Int. Cl.

| | |
|---|---|
| ***A61B 18/02*** | (2006.01) |
| ***A61B 17/00*** | (2006.01) |
| ***A61B 17/34*** | (2006.01) |

(52) U.S. Cl.
CPC .... *A61B 17/3496* (2013.01); *A61B 17/00234* (2013.01); *A61B 18/02* (2013.01)

(58) Field of Classification Search
CPC ................ A61B 18/02; A61B 17/2496; A61B 17/00234
See application file for complete search history.

(56) References Cited

U.S. PATENT DOCUMENTS 3,332,766 A * 7/1967 Ambrogi ................. C03B 7/086 65/356
2008/0200910 A1* 8/2008 Burger ................... A61B 18/02 604/113

* cited by examiner

*Primary Examiner* — Boniface N Nganga
(74) *Attorney, Agent, or Firm* — Gugliotta & Gugliotta LPA

(57) ABSTRACT

The present invention relates to a medical sheath apparatus designed to enhance minimally invasive procedures, particularly for nerve ablation using an approximately 20-gauge needle. The sheath incorporates a distal aspect with a ventilation system, a proximal sheath flaring for needle accommodation, and a female connection for needle engagement. Cold dissipators manage temperature during procedures. The apparatus streamlines the process, requiring only one skin penetration and soft tissue tunnel, reducing patient discomfort, enhancing accuracy, and shortening procedure times. Additionally, a method is provided, involving needle withdrawal, ultrasound-guided nerve identification, and local anesthesia administration, all within the sheath. This innovation offers a versatile solution applicable to various needle sizes and anatomical locations, significantly improving minimally invasive medical interventions.

8 Claims, 2 Drawing Sheets

SINGLE-PENETRATION SHEATH FOR MINIMALLY INVASIVE MEDICAL PROCEDURES

RELATED APPLICATIONS

The present invention claims benefit of U.S. Provisional Application 63/419,043 filed 25 Oct. 2022, and incorporated by reference as if fully rewritten herein.

BACKGROUND OF THE INVENTION

1. Field of the Invention

The present invention relates to medical devices and methods used in minimally invasive medical procedures requiring anesthetizing and treating nerves and, more specifically, to a sheath designed to streamline the process of anesthetizing and treating nerves and reducing the number of penetrations required and minimizing soft tissue trauma.

2. Description of the Related Art

Conventional medical procedures involving the administration of local anesthesia and nerve treatment often require multiple penetrations with needles, resulting in patient discomfort, increased procedure time, and soft tissue trauma. Currently, the Iovera® procedure is an example of such an existing method of targeted cyroanalgesia for pain relief using a needle and requires several sticks with a needle to anesthetize the skin. By way of example, and not meant as a limitation, such a procedure is exemplified in U.S. Pat. Nos. 8,298,216, 9,907,693, 9,072,478 and others, incorporated by reference as if fully rewritten herein.

Because of multiple needle sticks to nerves in performing the actual procedure, unnecessary soft tissue trauma and discomfort results. The current technique also requires the creation of multiple soft tissue tunnels as more than one needle is used throughout the procedure. For example, currently the Iovera® procedure uses the "Smart Tip 109, 309 and/or 2190 needle" which does not have a sheath, and the procedure requires multiple penetrations of the skin. See, for example, https://www.iovera.com/smart-tips. At the same time the nerves often must be re-identified via ultrasound causing undue trauma to the soft tissues and increases procedure time.

Further, the existing technology such as the Iovera® procedure with the 190 (or 2190) needle involves numerous needle sticks for skin numbing, nerve identification, and the actual treatment, leading to inefficiency and reduced accuracy.

Consequently, a need has been felt to overcome the shortcomings of existing procedures by facilitating a process using a single penetration.

SUMMARY OF THE INVENTION

It is thus objects of the present invention to provide an apparatus and method that address the shortcomings of existing procedures by providing a sheath-based system that facilitates the entire process from skin numbing to nerve ablation using a single penetration.

Briefly described the present invention, a medical sheath apparatus is provided that is adapted to enhance minimally invasive procedures, particularly for nerve ablation using a 190-gauge needle. The sheath incorporates a distal aspect with a ventilation system, a proximal sheath flaring for needle accommodation, and a female connection for needle engagement. Cold dissipators manage temperature during procedures. The apparatus streamlines the process, requiring only one skin penetration and soft tissue tunnel, reducing patient discomfort, enhancing accuracy, and shortening procedure times.

Additionally, a method is provided, involving needle withdrawal, ultrasound-guided nerve identification, and local anesthesia administration, all within the sheath. Such a versatile solution may further be applicable to various needle sizes and anatomical locations, significantly improving minimally invasive medical interventions.

It is an advantage of the present invention to utilize a single soft tissue tunnel, thereby minimizing tissue trauma and pain and enhancing patient comfort.

It is another advantage of a single skin penetration and soft tissue tunnel to result in shorter procedure times.

It is yet another advantage of the present invention to accommodate ultrasound-guided procedures and thereby enhance precision in nerve identification and treatment.

Additionally, the present invention is adaptable for use with different needle sizes, making it suitable for various medical interventions.

Further objects, features, elements and advantages of the invention will become apparent in the course of the following description.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

The best mode for carrying out the invention is presented in terms of its preferred embodiment, herein depicted within the Figures. It should be understood that the legal scope of the description is defined by the words of the claims set forth at the end of this patent and that the detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

The best mode for carrying out the invention is presented in terms of its preferred embodiment, herein depicted within the Figures.

1. Detailed Description of the Figures

Figure 1:
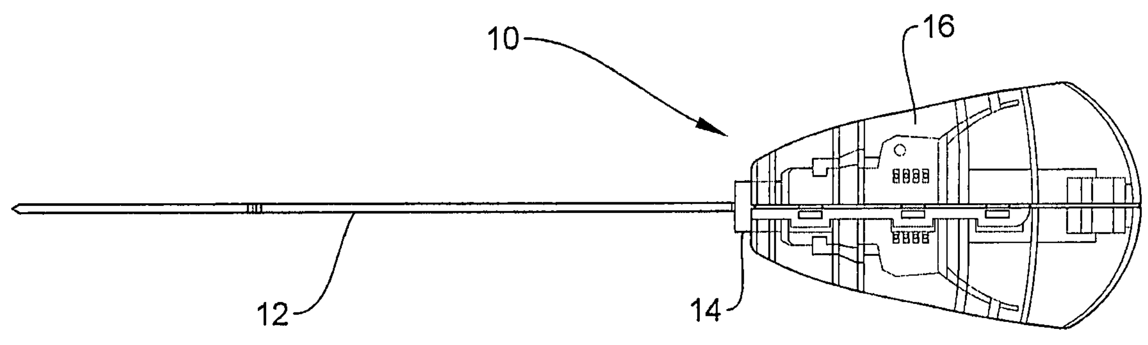
FIG. 1 depicts a Iovera® cryogenic needle device according to the PRIOR ART.

For clarity of description, the best mode of the present invention may be more easily envisioned as an improvement in conjunction with an Iovera® cryogenic needle device, generally noted as 10 and as shown in FIG. 1 according to the PRIOR ART, which is a medical instrument designed to provide targeted pain relief through the application of extreme cold temperatures. Such a device is for cryoneurolysis procedures, a minimally invasive technique that uses cold temperatures to temporarily numb or disable nerves, offering relief from pain and discomfort.

The Iovera® cryogenic needle device 10 typically consists of a needle 12, a connector 14, a cryogenic source 16, and a temperature control mechanism (not shown). The core component of the device is a specialized needle 12, often with a thin and elongated design. The needle 12 is designed to deliver extremely cold temperatures to a specific nerve or target area. The needle 12 is attached to a connector 14, which may be part of a console or handheld device that controls the temperature and the flow of the cryogenic gas. The device 10 is then connected to a cryogen source that provides the cooling agent, usually nitrous oxide or a similar gas. This source supplies the extremely cold temperatures required for the procedure. A temperature control mechanism is also provided to allow medical professionals to precisely regulate the cooling process. This ensures accurate and controlled application of cold temperatures to the target nerve.

Figure 2:
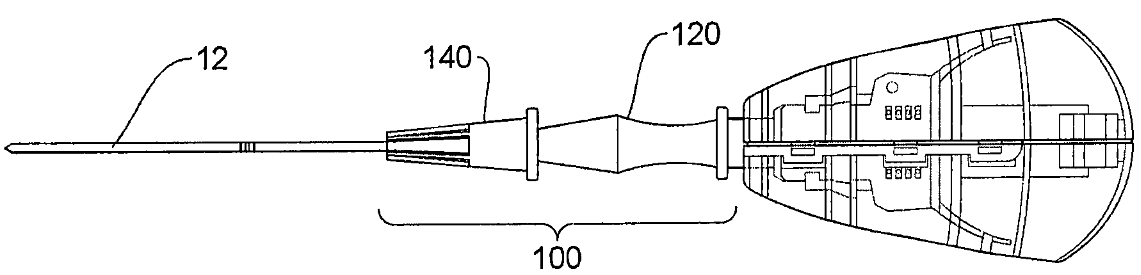
FIG. 2 depicts the Iovera® cryogenic needle device utilizing an improved sheath assembly in accordance with a preferred embodiment of the present invention.
Figure 3:
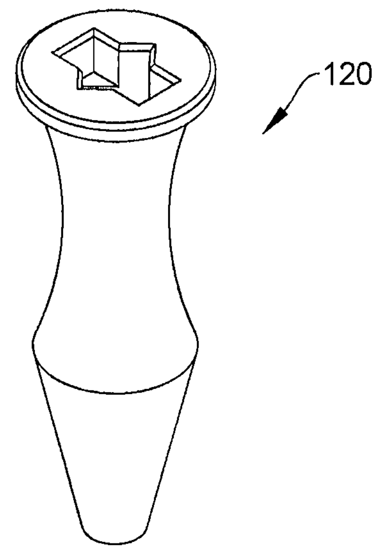
FIG. 3 is a perspective view of a connector element of the sheath assembly according to the preferred embodiment of the present invention.
Figure 4:
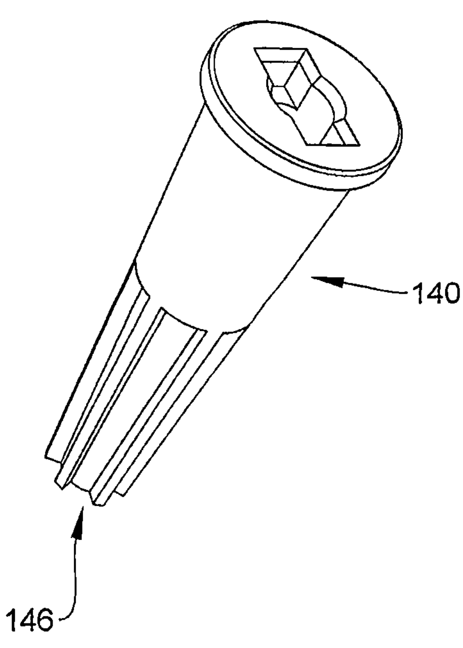
FIG. 4 is a perspective view of sheath dissipater element for use therewith.

Referring in conjunction with FIG. 2 through FIG. 4, wherein like reference numerals indicate the same parts throughout the several views, an improved sheath assembly, generally noted as 100, is provided specifically designed for use with the Iovera® procedure involving an approximately 20-gauge needle 12. The sheath assembly 100 may include a connector element 120 and a sheath 140. The connector element 120 may be positioned proximally, and the sheath 140 may be positioned distally.

The sheath 140 forms a tubular structure designed to fit the size of the 190/390/2190 needle 12 (approximately a 20-gauge needle). A plurality of ventilation vents 142 are formed to prevent condensation within the sheath 140. These vents 140 may be formed as fins for dissipation via radiation or may optionally form openings throughout the distal portion of the sheath 140 for dissipation via convection. Cold dissipators, including fin elements, may be located on both distal and proximal portions of the sheath to aid in temperature control during the procedure. The distal end 146 of the sheath 140 terminates approximately 0.5 mm proximal to the marking on the Iovera needle 12. The inner diameter of the sheath matches that of a 20-gauge needle, with a width of about 0.5 mm.

The connector element 120 connects the sheath 140 to the Iovera® needle. Two female components are interposed together, with one portion designed to engage the metal portion of the Iovera needle and the other portion for the long initial needle used for skin and nerve numbing. Molded to fit the proximal aspect of the Iovera needle, the connector element flares out to accommodate the needle 12.

The sheath assembly 100 may include two interposed female portions. The first matches the rectangular shape of the metal portion of the Iovera needle, while the second is designed to secure the initial long needle used for skin and nerve numbing.

While various materials may be used to form the various elements, it is envisioned that the connector element 120 may be a molded polymer material, while the sheath 140 may be metallic.

2. Operation of the Preferred Embodiment

In operation, local anesthetic medication is withdrawn with an 18-gauge needle into a 10 CC syringe. The 18-gauge needle is removed. A 22 gauge long spinal needle is attached to the 10 CC syringe. This spinal needle is then secured to the sheath assembly 100 via the female portion of the connector element 120. Ultrasound is used to identify the nerve to be treated. The skin is then prepped in a standard sterile fashion. The skin is then penetrated superficially to create a skin wheel to numb the skin. Once the skin is numb, the 22-gauge needle along with the sheath is then advanced to the previously mapped nerve. Local anesthesia is then administered over the nerve. The 22-gauge needle along with the 10 CC is removed while the sheath assembly remains in place. The Iovera needle is then placed into the sheath assembly and is secured using the female portion of the proximal end. The nerve is then treated with the needle. Once the Iovera cycle is complete, the needle along with the sheath is then removed.

The described invention provides a novel solution to the challenges posed by existing medical procedures involving needle-based interventions. By utilizing a specialized sheath design, the invention streamlines the procedure, reduces patient discomfort, and enhances procedural accuracy. This present invention is not limited to the Iovera® procedure alone. It can be adapted for use with various needle sizes and can be applied to different anatomical locations that require similar needle-based interventions.

The claimed invention differs from what currently exists. Prior to this invention there is no sheath that covers the needle. This invention gives the ability to inject the skin, locate the nerve via ultrasound, numb up the nerve with anesthetic and finally perform the procedure with the IOVERA needle with one puncture of the skin and soft tissue tunnel. Currently the IOVERA needle procedure is inefficient due to multiple sticks being made decreasing accuracy and increasing the time of the procedure. Further, the present invention decreases procedure time and minimizes soft tissue trauma by completing the entire procedure with one penetration of the skin and soft tissues.

The foregoing descriptions of specific embodiments of the present invention are presented for purposes of illustration and description. The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples, and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein but to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way. Any unintended embracement of such subject matter is hereby disclaimed. They are not intended to be exhaustive nor to limit the invention to precise forms disclosed and, obviously, many modifications and variations are possible in light of the above teaching. The embodiments are chosen and described in order to best explain principles of the invention and its practical application, to thereby enable others skilled in the art to best utilize the invention and its various embodiments with various modifications as are suited to the particular use contemplated. It is intended that a scope of the invention be defined broadly by the Drawings and Specification appended hereto and to their equivalents. Therefore, the scope of the invention is in no way to be limited only by any adverse inference under the rulings of *Warner-Jenkinson Company*, v. *Hilton Davis Chemical,* 520 US 17 (1997) or *Festo Corp*. v. *Shoketsu Kinzoku Kogyo Kabushiki Co.,* 535 U.S. 722 (2002), or other similar caselaw or subsequent precedent should not be made if any future claims are added or amended subsequent to this Patent Application.

What is claimed is:

1. A medical sheath apparatus for facilitating a minimally invasive procedure, comprising:

a distal aspect with a ventilation system comprising multiple openings to prevent condensation within the sheath;

a proximal sheath flaring out to accommodate a medical needle;

a female portion of connection located on the proximal sheath for engaging said medical needle;

fin elements for cold dissipation located on both the distal and proximal portions of the sheath, wherein the multiple openings are distinct from the fin elements and both the multiple openings and the fin elements are configured to prevent condensation within the sheath.

2. The medical sheath apparatus of claim 1, wherein the distal aspect of the sheath terminates approximately 0.5 mm proximal to a marking on a medical needle.

3. The medical sheath apparatus of claim 1, wherein the inner diameter of the distal aspect of the sheath is equivalent to a 20-gauge needle.

4. The medical sheath apparatus of claim 1, wherein the sheath has a thickness of approximately 0.5 mm.

5. The medical sheath apparatus of claim 1, wherein multiple openings are distributed throughout the entire distal portion of the sheath.

6. The medical sheath apparatus of claim 1, wherein the ventilation system includes deeper vents on the proximal portion of the sheath, connecting to an inner portion of the female connection.

7. The medical sheath apparatus of claim 1, wherein the female portion of the connection includes two interposed female components, a first component matching a shape of a metal portion of the medical needle and a second component designed to engage a long spinal needle.

8. The medical sheath apparatus of claim 1, wherein the fin elements for cold dissipation are configured to manage temperature during a medical procedure.

* * * * *